US009892620B2

(12) United States Patent
Kramer

(10) Patent No.: US 9,892,620 B2
(45) Date of Patent: Feb. 13, 2018

(54) SYSTEM AND METHOD FOR PREVENTING TRANSFER OF INFECTIOUS DISEASE

(71) Applicant: Jordan L Kramer, East Rockaway, NY (US)

(72) Inventor: Jordan L Kramer, East Rockaway, NY (US)

(*) Notice: Subject to any disclaimer, the term of this patent is extended or adjusted under 35 U.S.C. 154(b) by 0 days.

(21) Appl. No.: 15/338,317

(22) Filed: Oct. 28, 2016

(65) Prior Publication Data

US 2017/0124850 A1 May 4, 2017

Related U.S. Application Data

(60) Provisional application No. 62/248,016, filed on Oct. 29, 2015.

(51) Int. Cl.
| | |
|---|---|
| G08B 21/24 | (2006.01) |
| G06F 19/00 | (2011.01) |
| G08B 5/36 | (2006.01) |
| G08B 21/18 | (2006.01) |
| G08B 21/02 | (2006.01) |
| G09B 19/00 | (2006.01) |

(52) U.S. Cl.
CPC ....... *G08B 21/245* (2013.01); *G08B 21/0277* (2013.01); *G08B 21/0288* (2013.01); *G08B 21/0294* (2013.01); *G06F 19/325* (2013.01); *G06F 19/327* (2013.01); *G08B 5/36* (2013.01); *G08B 21/02* (2013.01); *G08B 21/18* (2013.01); *G09B 19/0076* (2013.01)

(58) Field of Classification Search
CPC ...... G08B 21/245; G08B 21/18; G08B 21/02; G08B 5/36; G06F 19/327; G06F 19/325; G06F 19/0076; G09B 19/0076
See application file for complete search history.

(56) References Cited

U.S. PATENT DOCUMENTS

| | | | | |
|---|---|---|---|---|
| 2014/0180713 | A1* | 6/2014 | Tenarvitz | G06F 19/327 705/2 |
| 2014/0266692 | A1* | 9/2014 | Freedman | G08B 21/245 340/539.11 |
| 2016/0095063 | A1* | 3/2016 | Vigier | H04W 52/0229 455/574 |
| 2016/0350639 | A1* | 12/2016 | Tere | A45C 11/00 |
| 2017/0124366 | A1* | 5/2017 | Good | G06K 7/10425 |

* cited by examiner

*Primary Examiner* — Benyam Haile
(74) *Attorney, Agent, or Firm* — Grumbles Law PLLC; Brittany Nanzig; Paul Feng

(57) ABSTRACT

A system and method to assist in the prevention of the transfer of infectious diseases. More particularly, a system and method that monitors and alerts caregivers to cleanse, sanitize, and/or wash their hands prior to engaging with other individuals in their care. The disclosed technology includes beacons in wireless communication with a mobile computing device, such as a smart phone, that monitors, alerts and reports on compliance by caregivers and other healthcare workers to ensure that they routinely cleanse, sanitize and/or wash their hands prior to and after contacting a patient at a hospital, nursing home, clinic, office and/or similar environment. The beacons are located in a patient's wristband and in a disinfectant dispenser. The disclosed technology can monitor the patient at all times the patient is in the healthcare facility.

10 Claims, 17 Drawing Sheets

FIG. 17

SYSTEM AND METHOD FOR PREVENTING TRANSFER OF INFECTIOUS DISEASE

CROSS-REFERENCE TO RELATED APPLICATION

This application claims the benefit of U.S. Provisional Application No. 62/248,016 filed Oct. 29, 2015 and titled SYSTEM AND METHOD OF MONITORING AND ALERTING HEALTHCARE WORKERS TO HELP PREVENT TRANSFER OF INFECTIOUS DISEASE.

FIELD OF THE TECHNOLOGY

The present disclosure relates to a system and method that assists in the prevention of the transfer of infectious diseases.

BACKGROUND OF THE INVENTION

The prevention of transferring infectious diseases is a major and ongoing concern in hospitals and similar environments where care and treatments are provided to those that suffer from any disease process. In the healthcare industry, it is an accepted fact that good hand hygiene is of paramount importance in preventing the spread of infectious diseases. There is substantial data to support the fact that infectious diseases are transmitted after routine activities involving direct contact between healthcare workers and patients and then direct contact between the same healthcare workers and other patients before the healthcare workers have sanitized or washed their hands. By the same token, transmission of infectious diseases may also take place via indirect contact by touching contaminated surfaces or clothing, as well as wheelchairs and bed rails used to transport patients.

As a result of the transmission of infectious diseases at hospitals, a significant percentage of patients admitted to the facility develop hospital-acquired infections (HAI) that are unrelated to their initial reason for admission. This adds a further strain upon, and causes an expenditure of resources necessary to treat, these patients. Even more troublesome is the fact that thousands of these patients who acquire infections at hospitals die each year.

To help solve the problem, many healthcare facilities have instituted policies and practices that encourage healthcare workers to practice good hygiene and wash their hands. However, compliance with these policies is well below par. Even when objective monitoring and/or direct observation is instituted by a facility utilizing, for example, a nurse manager or infection control practitioners, reliability and compliance remains less than optimal. Therefore, a system is needed that can increase compliance with good hygiene policies.

SUMMARY OF THE INVENTION

The present disclosure is to a system and method to assist in the prevention of the transfer of infectious diseases. More particularly, the disclosed technology involves a system and method that monitors and alerts caregivers to cleanse, sanitize, and/or wash their hands prior to engaging with other individuals in their care. Even more specifically, the disclosed technology includes beacons in wireless communication with a mobile computing device, such as a smart phone, that monitors, alerts and reports on compliance by caregivers and other healthcare workers to ensure that they routinely cleanse, sanitize and/or wash their hands prior to and after contacting a patient at a hospital, nursing home, clinic, office and/or similar environment. The beacons are located in a patient's wristband and in a disinfectant dispenser. The disclosed technology can monitor the patient in and beyond the closed space of an individual room (i.e. at all times the patient is in the hospital).

BRIEF DESCRIPTION OF THE DRAWINGS

FIG. 17 is an exemplary hospital report that includes a visual overview of the information in the form of charts that is time-stamped.

DETAILED DESCRIPTION

Figure 9:
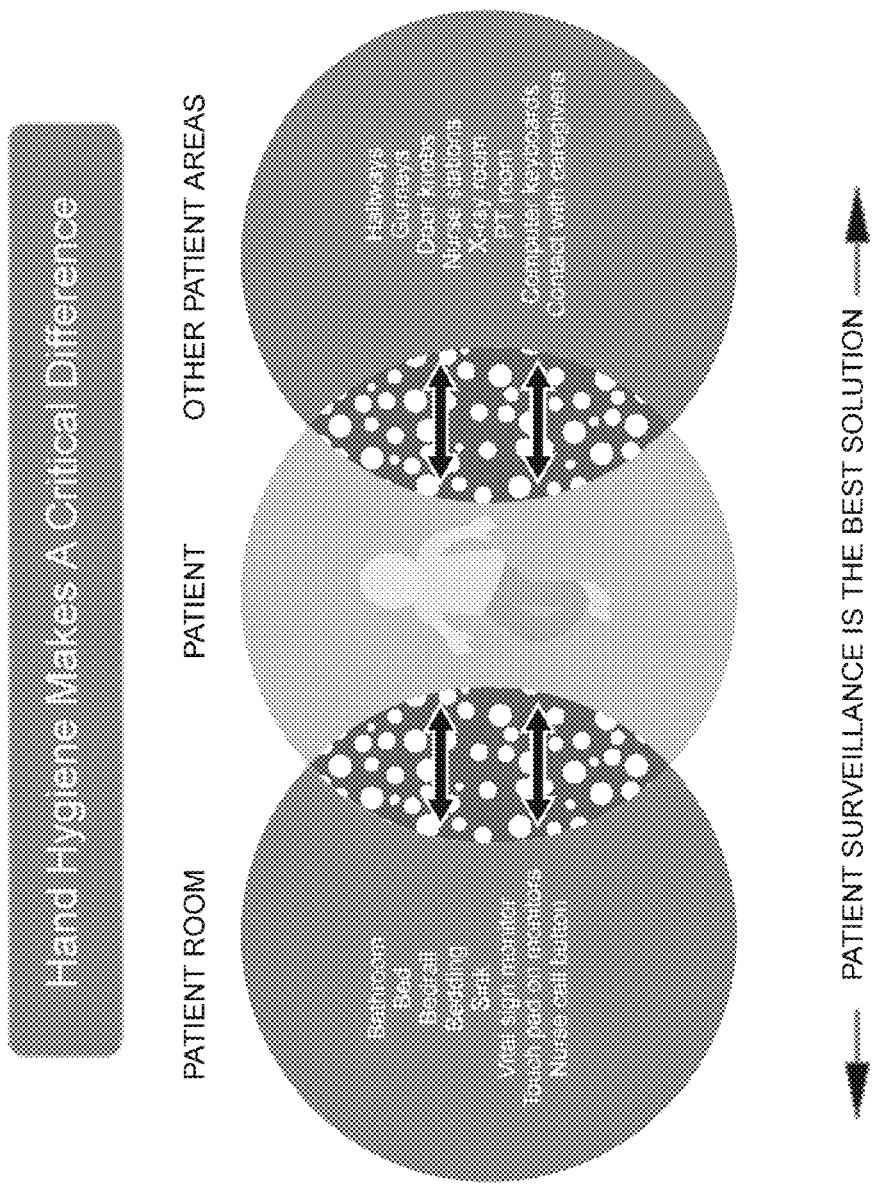
FIG. 9 illustrates the ease with which infection can spread by a caregiver in a healthcare facility.

In view of the difficulty in getting healthcare workers to practice good hand hygiene, despite the ease with which hospital-acquired infections can knowingly be transmitted, as illustrated in FIG. 9, a system and corresponding method are disclosed to monitor and alert healthcare workers to cleanse, sanitize and/or wash their hands prior to, and after engaging, individuals or patients in their care. The system and methods disclosed herein include reporting of hand hygiene compliance by healthcare workers.

With reference to FIG. 1 through FIG. 4, the system of the present system comprises one or more computer servers operated by machine-readable software instructions present on non-transitory computer readable storage media to perform a variety of functions. With respect to the computer hardware of the system, CPU-based hardware, computers, and/or servers are arranged to communicate with one another and with one or more databases and/or data stores, preferably residing therein, which are used to store data of the types described herein. When and after data is stored, the servers and software parse and filter the data pursuant to encoded instructions to allow a user to search for specific data. In addition to using on-site hardware and software, it should be appreciated that data may be stored, and the software with program instructions on non-transitory hardware storage media described herein, may be implemented, virtually or otherwise, utilizing secure services provided by a third party service. Moreover, one or more relational databases are implemented for storing information regarding patient beacon bracelets, hygienic dispensers, hospitals, patients, healthcare workers/caregivers, and one or more relationships between them as well additional data, metadata and algorithms, emergency contact numbers and allergy information. The one or more databases also store the mobile application user credentials and analytics data. Additional details pertaining to the hardware are provided below.

Figure 10:
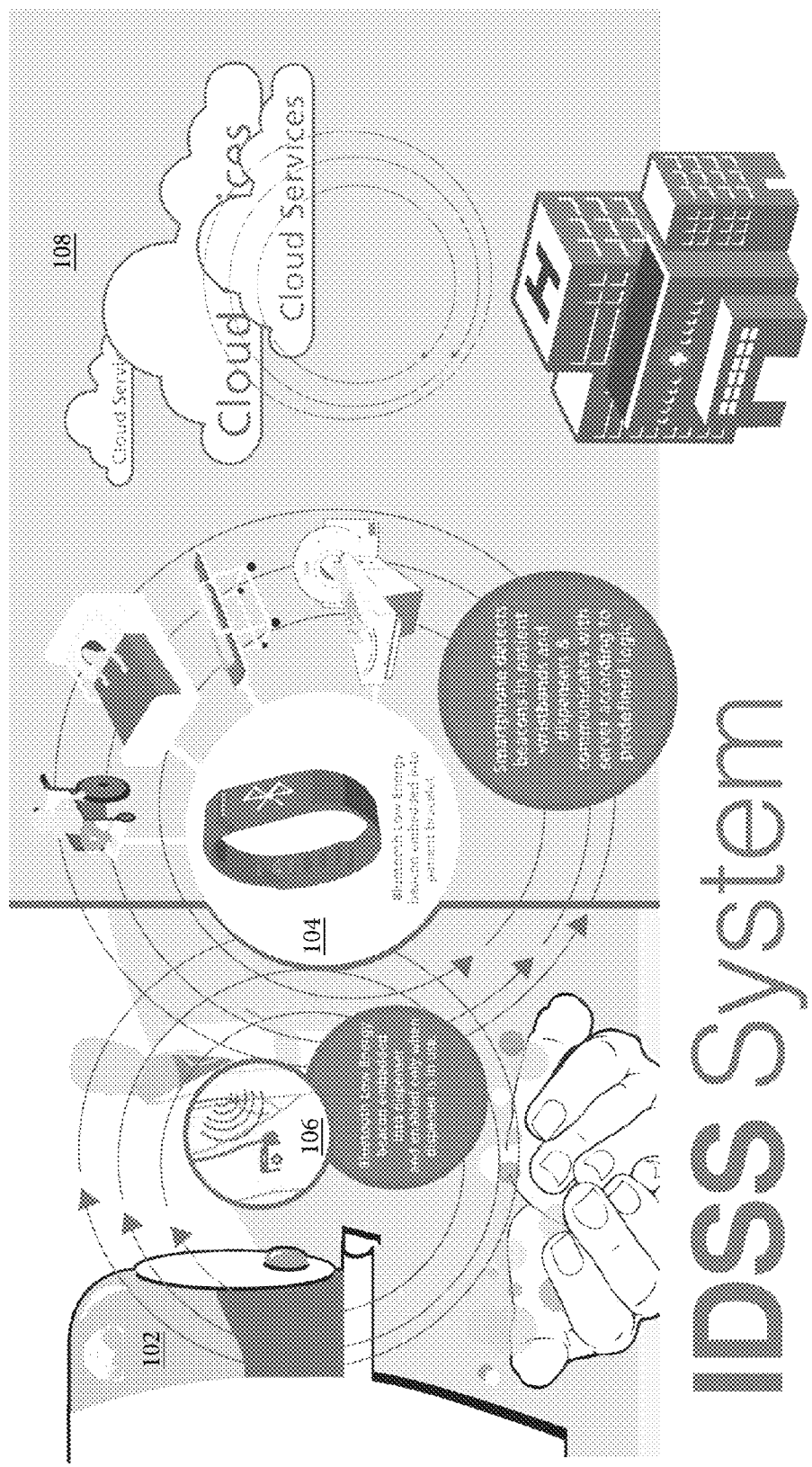
FIG. 10 illustrates the various components of one embodiment of the disclosed invention.
Figure 11:
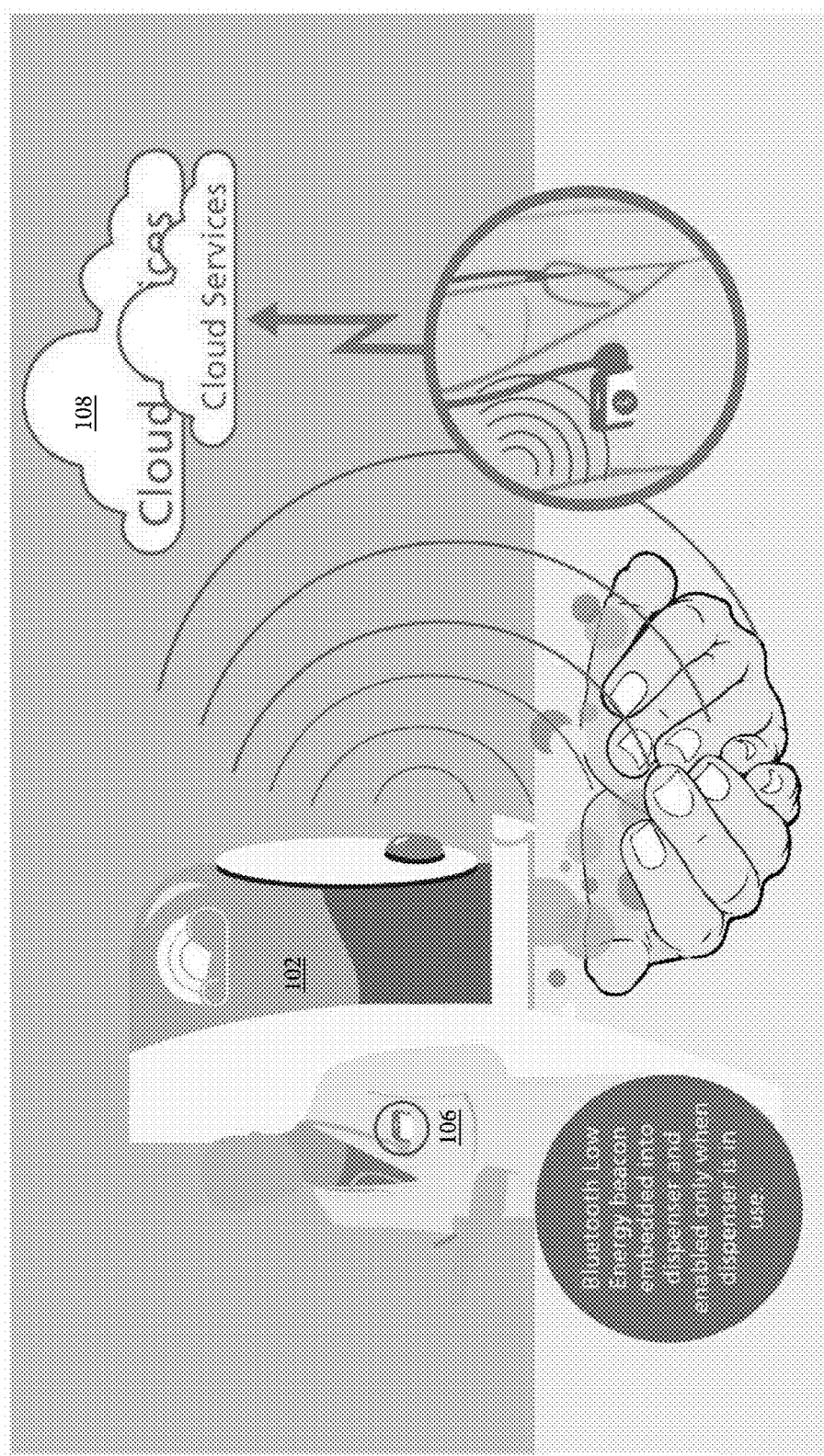
FIG. 11 illustrates how the various components of the disclosed invention communicate to each other.

Generally, the disclosed system includes a Bluetooth low energy beacon 102 embedded into, on, or within a few inches of a hands-free sanitizer or soap dispenser, wherein the beacon is enabled when the dispenser is in use. As illustrated in FIGS. 10 and 11, the system may also include a second Bluetooth low energy beacon 104 that is embedded into a patient wristband or hospital bracelet and a computing device hosting a mobile application 106 that can detect the beacons 102, 104 in patient wristbands and soap/sanitizer dispensers and communicate with the beacons 102, 104 and with a server 108 according to predefined logic. This communication can be recorded in the cloud 108 in order to facilitate further data analytics.

Upon detecting a beacon 102 embedded into a disinfection material dispenser, the caregiver's mobile application 106, which can be installed on the caregiver's mobile device, can report a disinfection action to the server 108. Based on the disinfection of hands or lack thereof and the logic regarding approaching and departing from patients, compliance or non-compliance is reported to the cloud server 108 by the caregiver's mobile application 106.

Figure 1:
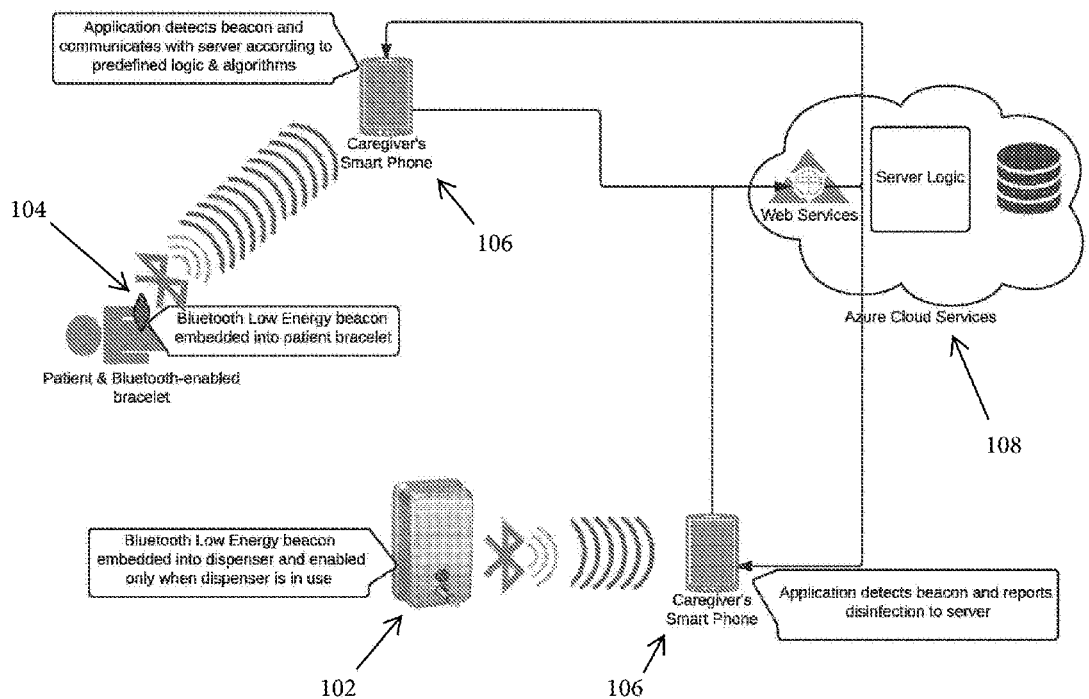
FIG. 1 is a system diagram illustrating beacon detection and reporting as well as patient bracelet beacon association
Figure 1:
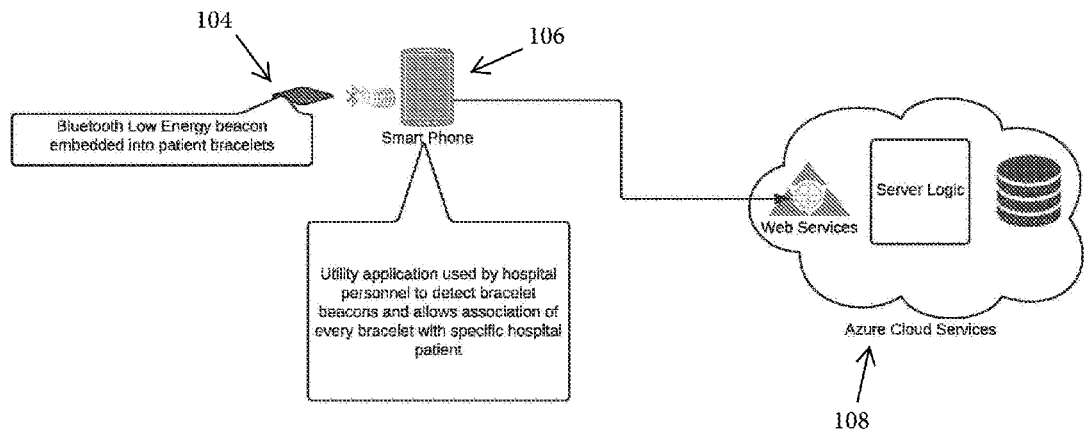

FIG. 1 is a system diagram illustrating beacon detection and reporting, via a network, to the backend of the system 108 where data is stored, as well as patient bracelet beacon 104 association. The caregiver's mobile application 106 on the caregiver's mobile device can constantly scan for Bluetooth low energy beacons. Upon detecting a beacon 104 embedded into a bracelet worn by a patient, the mobile application 106 can display a notification and sound a warning if the caregiver has not recently disinfected his/her hands. When the caregiver departs from the patient, if the caregiver does not disinfect his/her hands before moving a distance D1 from the patient, a warning is displayed and sounded. To determine the caregiver's location, the mobile application 106 may utilize a global positioning system (GPS) or wireless tracking feature. The patient's beacon 104 may also transmit its relative location, so that the mobile application 106 can compare the location of the patient's beacon 104 to the location of the caregiver's mobile application 106. In some embodiments, the caregiver's mobile device has a beacon, in which case the mobile device beacon can have its own GPS or wireless tracking device.

Figure 2:
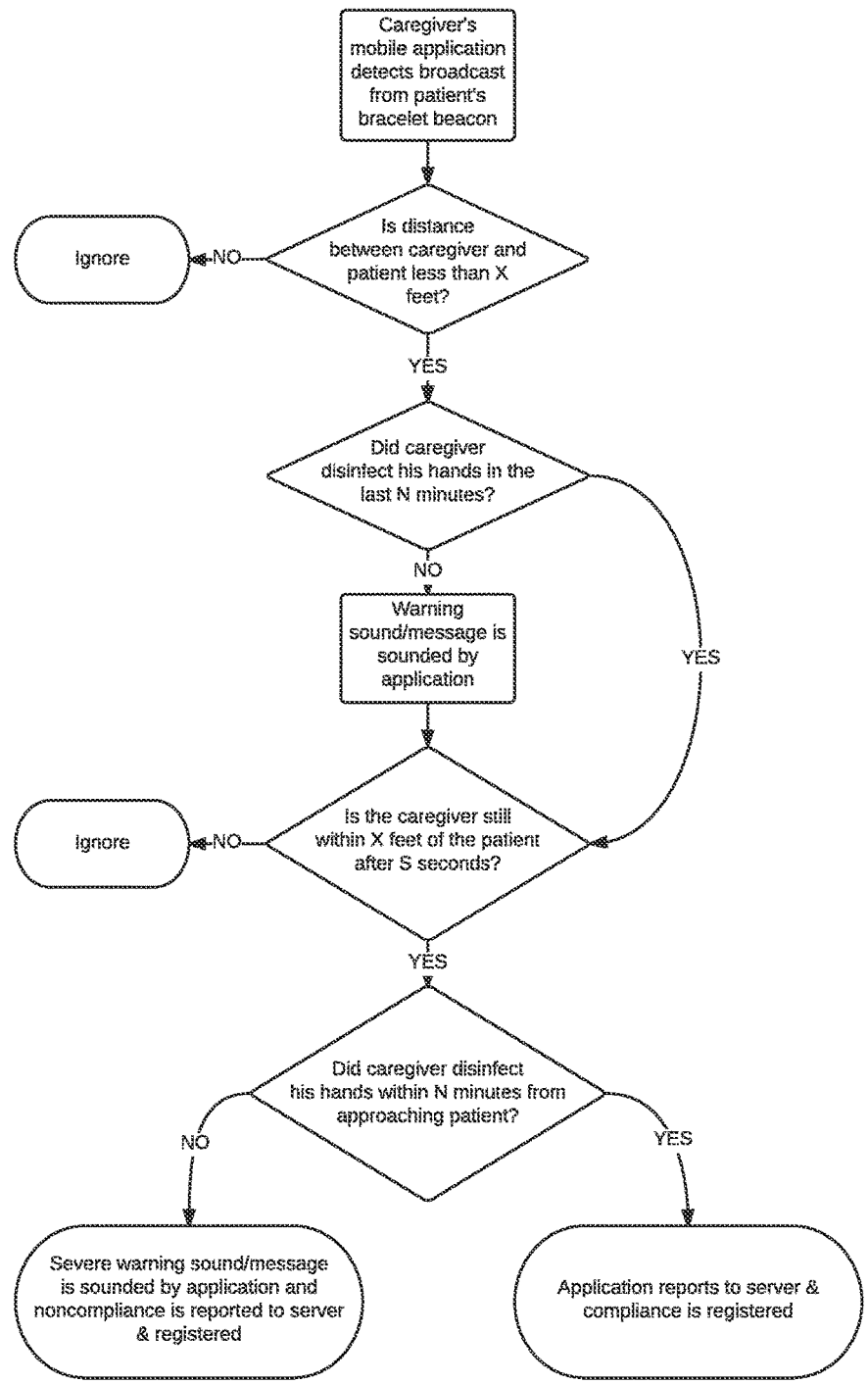
FIG. 2 is a flowchart illustrating an exemplary process for detecting a patient's beacon on approach by a healthcare worker and reporting compliance with disinfecting protocols.
Figure 3:
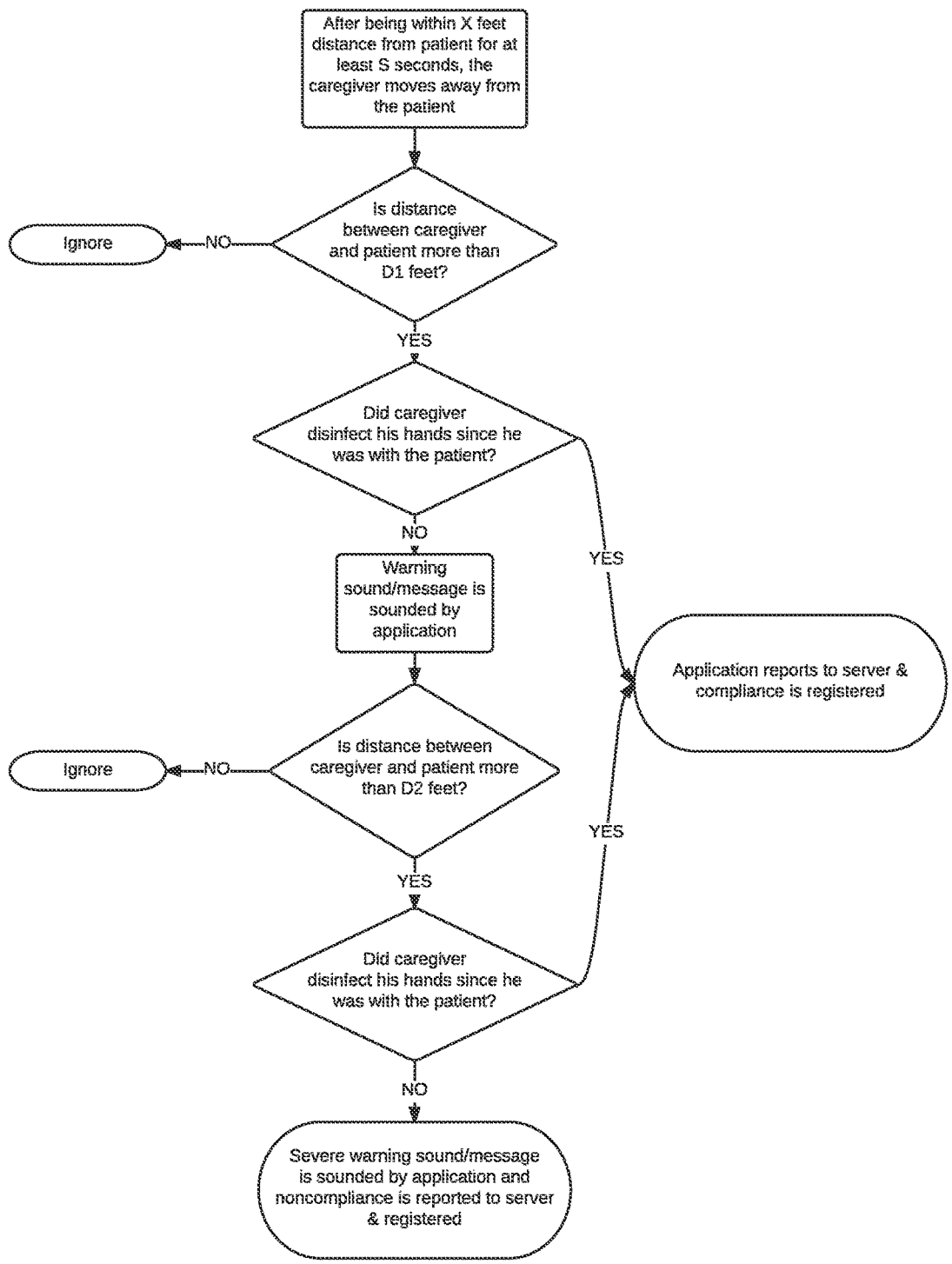
FIG. 3 is a flowchart illustrating an exemplary process that occurs when a caregiver departs from the vicinity of a patient.
Figure 4:
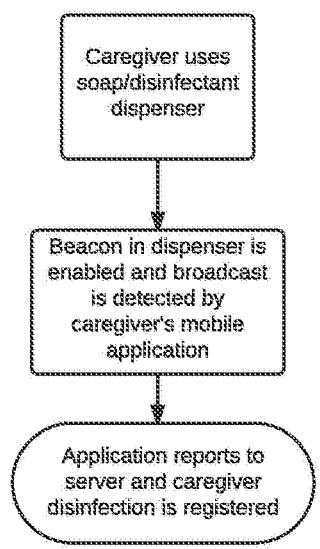
FIG. 4 is a flowchart illustrating an exemplary process that occurs when a caregiver uses a soap or disinfectant dispenser to disinfect the caregiver's hands.

With reference to FIG. 2 through FIG. 4, a hospital mobile application 106 enables designated staff or IT personnel to associate a beacon 104 with a single patient. This can occur through the use of a patient wristband with an embedded beacon 104. This association enables the tracking of compliance and non-compliance in interactions between caregivers and any particular patient. The association process is performed by entering the "beacon/patient pairing" mode of the mobile application 106. In this mode, the mobile application 106 scans for Bluetooth low energy beacons with the predefined UUID and, upon detection, displays information of one or more detected beacons. The designated hospital staff selects the correct beacon from the list and continues on to enter the patient's information. The beacon information (UUID, major, minor, mac address values) as well as the patient information are transmitted to the cloud server 108 via the cloud API and saved to the database.

Figure 12:
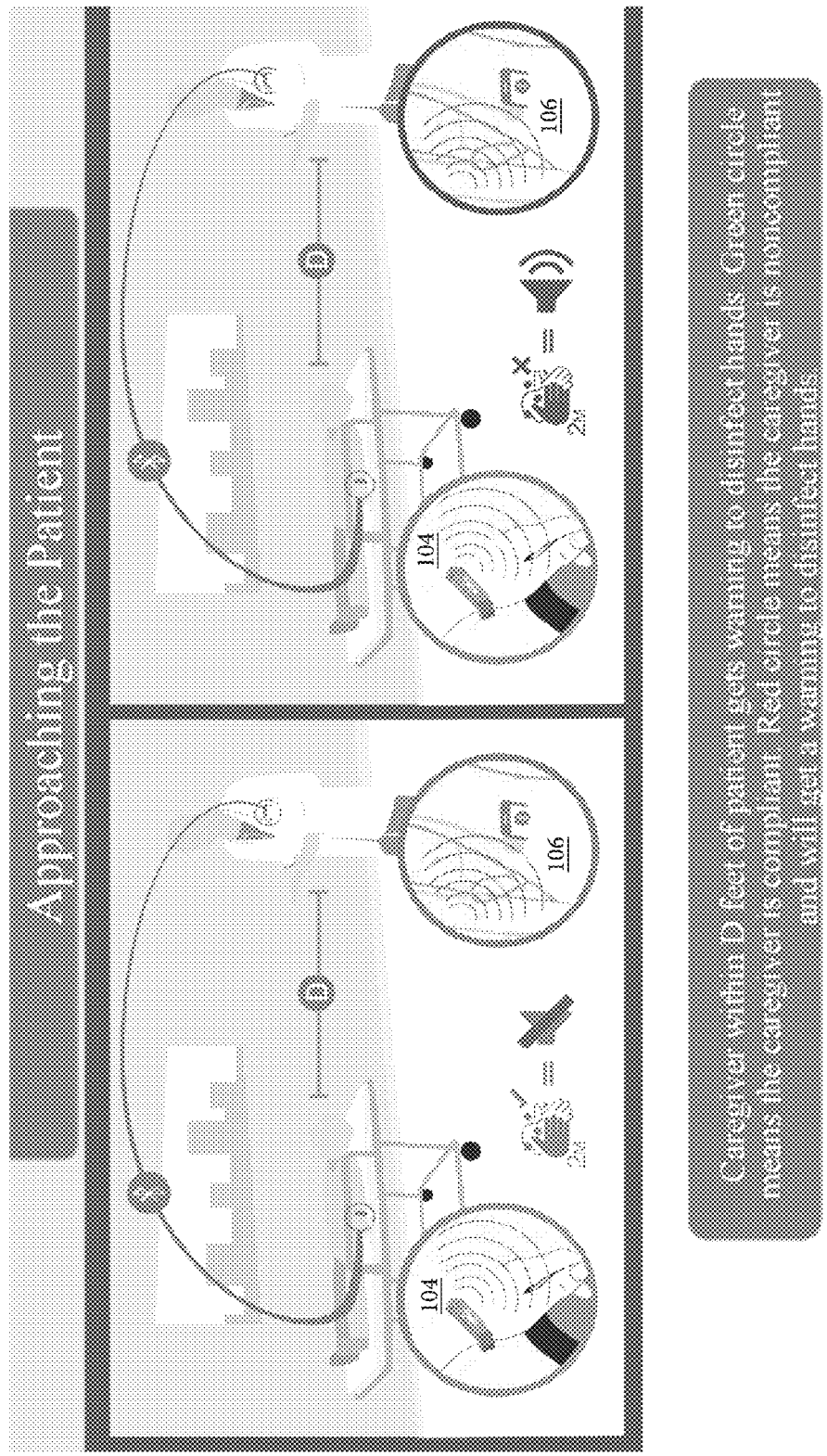
FIG. 12 illustrates the system detecting a patient's beacon on approach by a caregiver and reporting compliance with disinfecting protocols or warning to disinfect.

FIG. 2 is a flowchart illustrating an exemplary process for detecting a patient's beacon 104 on approach by a caregiver and reporting compliance with disinfecting protocols. FIG. 12 further illustrates this process. When a caregiver gets within X feet (for example, five feet) of a beacon wristband 104, if caregiver did not disinfect hands in the last N minutes (for example, two minutes), a warning beep is sounded. If the caregiver disinfected hands in the last N minutes, then no warning is sounded. If the caregiver is still within the X feet distance after S seconds (for example, 30 seconds), then if caregiver did not disinfect hands in the last N minutes, a more severe warning is sounded and non-compliance is registered. If caregiver did disinfect hands in the last N minutes, no warning is sounded and compliance is registered. It should be appreciated that the amount of distance and time can be customized and altered, as needed, depending on desired protocols and desired compliance for a particular facility, and, in some embodiments, the facility floor.

Figure 13:
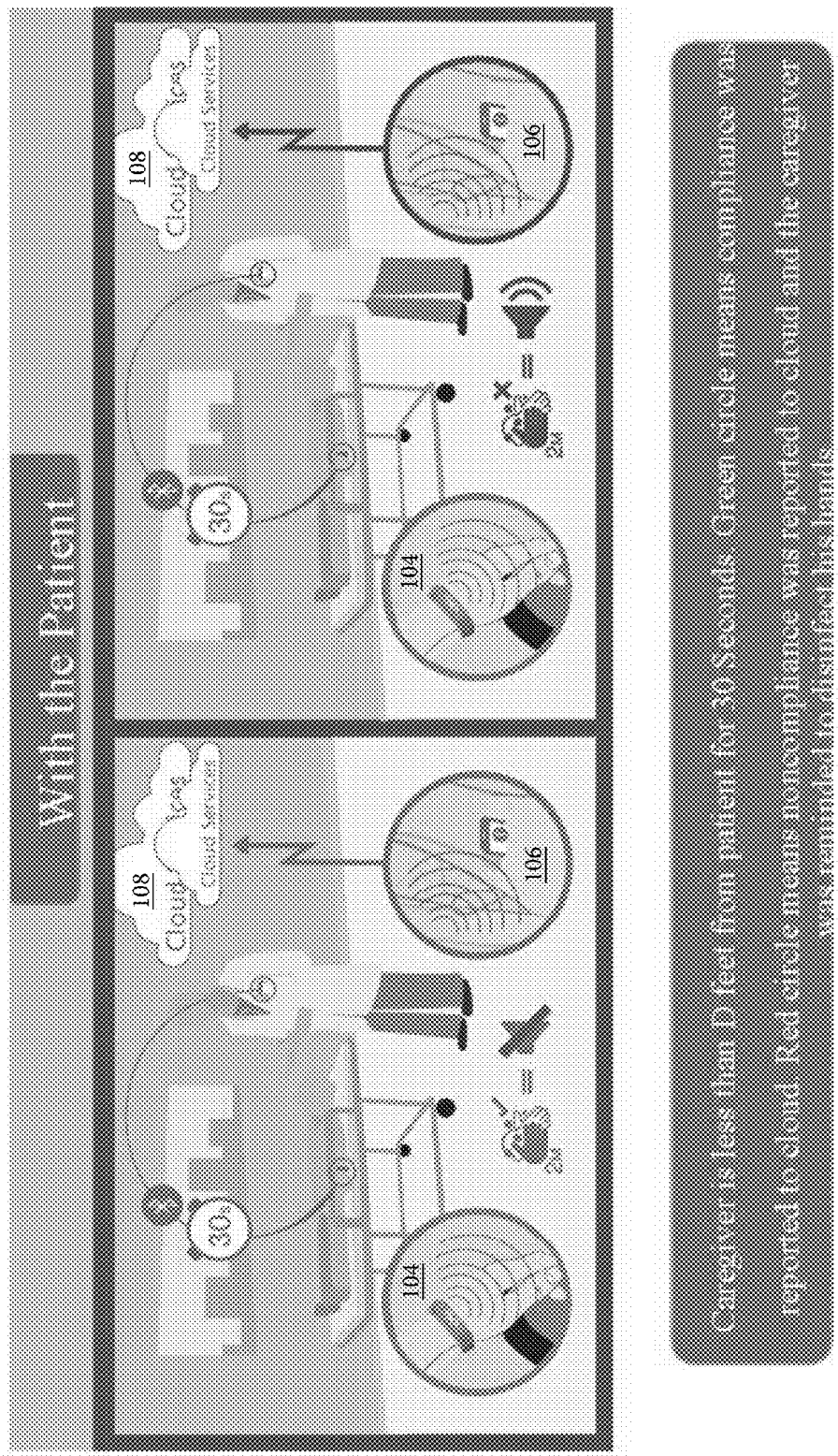
FIG. 13 illustrates the system detecting a patient's beacon as a caregiver is within the vicinity of a patient and reporting compliance or non-compliance to the cloud.

If the system mobile application 106 detects that the caregiver is within X feet from one or more additional patients for over s seconds, a special warning may be sounded reminding the caregiver to disinfect hands between treating the various patients, and the mobile application 106 will report the caregiver as having visited the one more additional patients. FIG. 13 illustrates this process. This may not appear in the report the caregiver can see, but it may appear in the hospital report in order to allow tracking of disease spreading.

Figure 14:
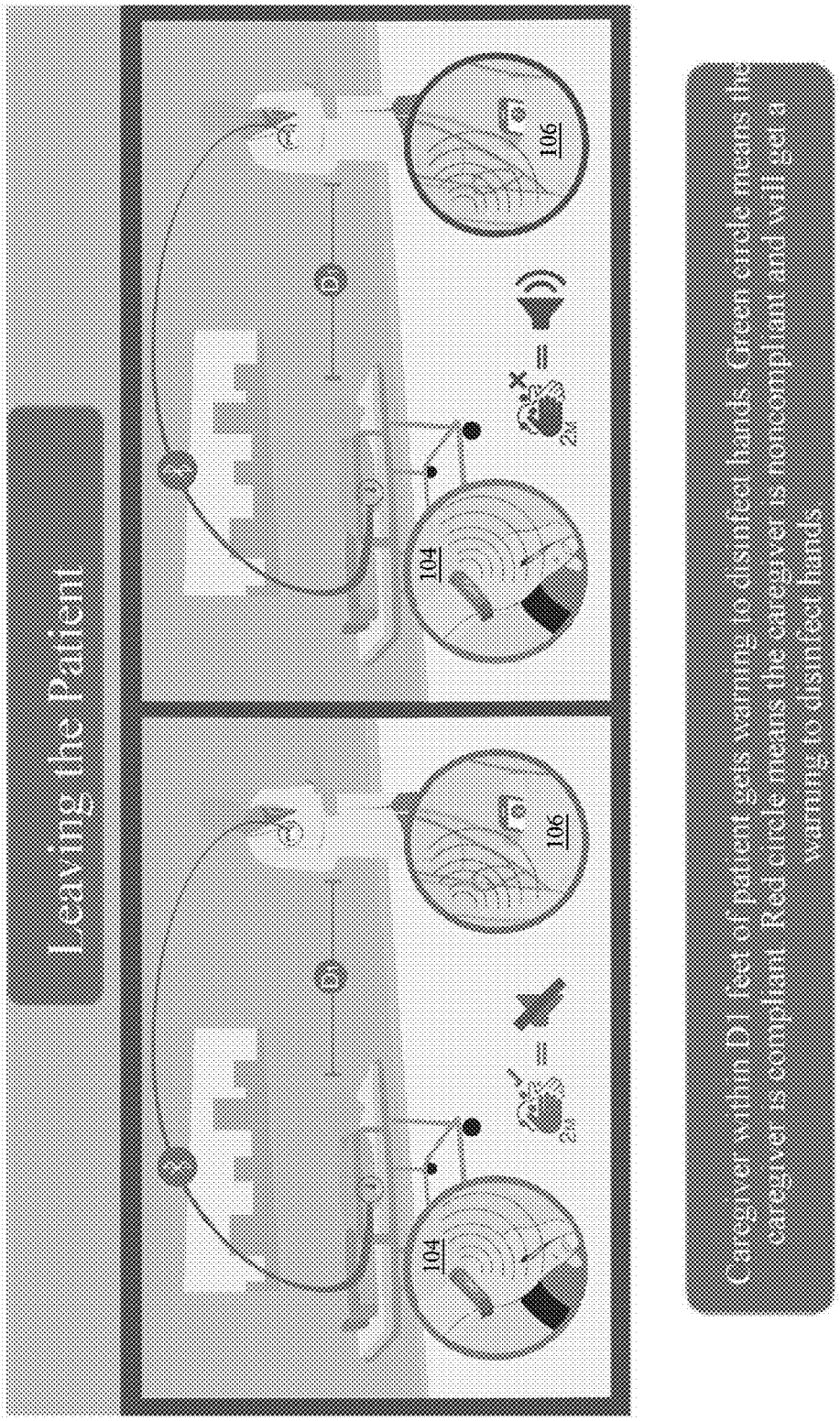
FIG. 14 illustrates the system detecting a patient's beacon when a caregiver departs from the vicinity of a patient and reporting compliance or warning caregiver to disinfect.
Figure 15:
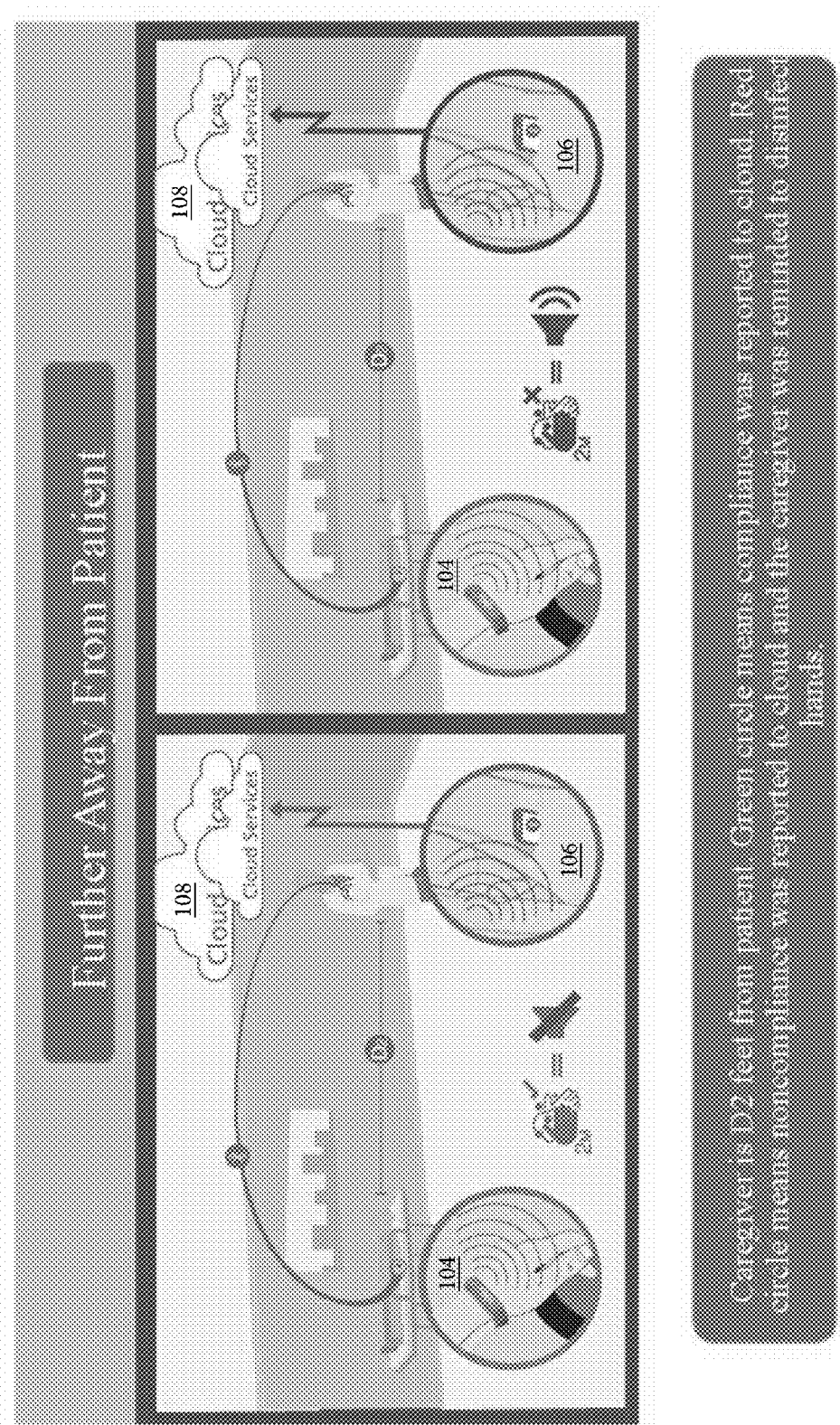
FIG. 15 illustrates the system detecting a patient's beacon when a caregiver is away from the vicinity of a recently visited patient and alerting the cloud of compliance or non-compliance.

FIG. 3 is a flowchart illustrating an exemplary process that occurs when a caregiver departs from the vicinity of a patient. FIGS. 14 and 15 further illustrates this process. After being within the X feet distance (for example, five feet) for at least S seconds (for example, 30 seconds), if the caregiver gets over D1 distance (for example, eight feet) from the beacon wristband 104, if the caregiver did not disinfect hands since being with the patient, a warning beep is sounded. Conversely, if the caregiver did disinfect hands since being with the patient, no warning is sounded. Further, if the caregiver is over D2 feet (for example, 15 feet) from the beacon bracelet 104 then, if caregiver did not disinfect hands since being with the patient, a more severe warning is sounded and non-compliance is registered. Conversely, if caregiver did disinfect hands since being with the patient, then no warning is sounded and compliance is registered.

Additionally, it should be appreciated that both compliance and non-compliance should be reported to the cloud 108. For example, reporting to the cloud 108 can occur by reporting all patient approaching and departing actions by the caregiver.

In some embodiments, a beacon 102 is fitted to or near a soap/sanitizer dispenser. Therefore, a soap/sanitizer dispenser fitted with a beacon 102 may broadcast when the soap/sanitizer dispenser is in use. More specifically, with reference to FIG. 4, once a caregiver uses a soap or disinfectant dispenser, the beacon in the dispenser 102 is enabled, a broadcast is made from the beacon 102, and the broadcast is detected by the caregiver's mobile application 106. When the mobile application 106 detects the broadcast, it can report to the cloud 108 and register the caregiver as having washed hands. At that point, the compliance is reported and registered on the server 108. The system can sound a confirmation message upon detecting the dispenser beacon 102 so that the caregiver knows the action has been registered.

The system and methods of the present disclosure are implemented in part via a series of graphical user interfaces (GUI), which can include various pages such as, but not limited to, a tutorial screen, a login screen 500, an end user license agreement (EULA) screen 600, a dashboard screen 700, and a compliance/non-compliance interaction details screen 800. Generally, the GUI paradigm is designed to enable a user to dig deeper into screen hierarchy. For example, a menu option can appear on all top-level screens, allowing for display of the menu and direct access to all top-level menu items. Additionally, all content screens that are displayed in tables or grids can have pull-to-refresh functionality.

Figure 5:
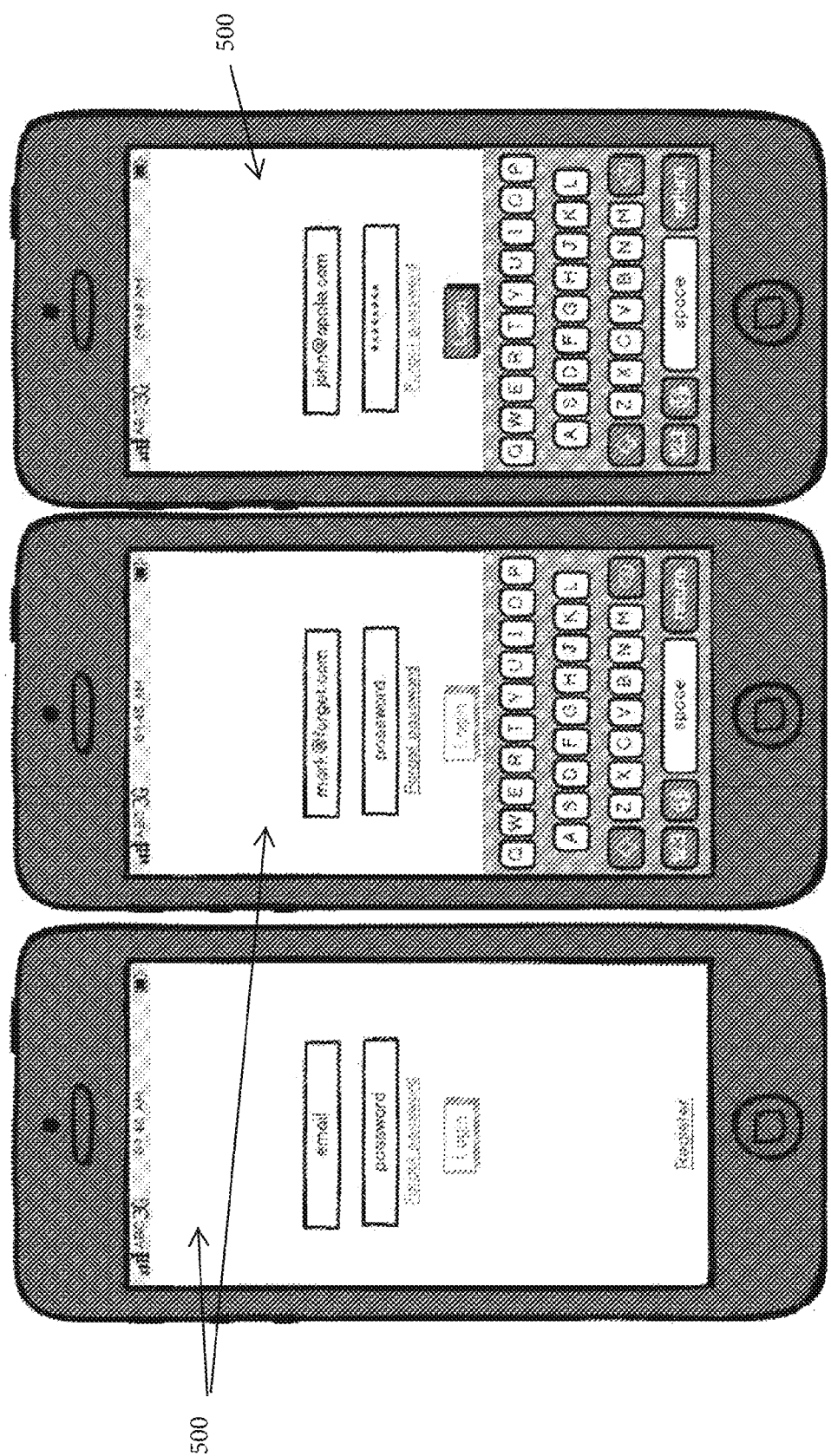
FIG. 5 is an example graphical user interface showing a mobile interface login screen according to one embodiment of the present disclosure.

In one embodiment of the disclosed system, the login screen 500, illustrated in FIG. 5, is the first screen displayed to the user after installation and/or opening of the mobile application 106 from closed mode. The login screen 500 may require input of an email and password for access to the mobile application 106. In some embodiments, the email and password are auto-generated by the mobile application 106 when the user's information is input into the system. For example, input of an email address may auto populate a corresponding password that a user can input into the mobile application 106 for access. Preferably, the email and password input fields are enabled to undergo data validation based on predefined criteria and, when a valid email and password are entered, the user can access additional features of the mobile application 106. If a valid email and password are not entered, the mobile application 106 may present the user with an appropriate error message. This error message may indicate that the entered information is not valid. Alternatively, it may indicate that the email and/or password are wrong or, if the user has not yet confirmed the email address, it may indicate the lack of confirmation.

In addition to the email and password input fields, a forgotten password input may be available to a user who remembers his or her email, but cannot recall his or her password. This feature is available for pre-existing email addresses and, after requesting password information, the system may send the password to the entered email address.

Figures 6, 7, 8:
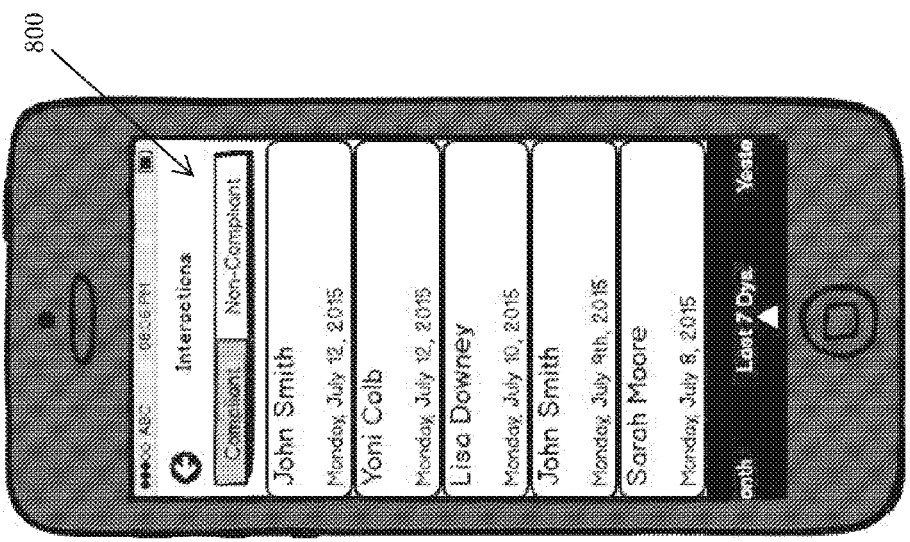
FIG. 6 is an example graphical user interface showing a mobile interface user end license agreement screen according to one embodiment of the present disclosure.
FIG. 7 is an example graphical user interface showing a mobile interface dashboard screen according to one embodiment of the present disclosure
FIG. 8 is an example graphical user interface showing a mobile interface compliance interaction details screen according to one embodiment of the present disclosure.

After the system validates the user's credentials, it can display a EULA screen 600, as illustrated in FIG. 6. When the user, in some embodiments, indicates acceptance of the EULA terms, the mobile application 106 will display a home screen or dashboard 700. Preferably, the user cannot access the home screen/dashboard 700 until the user has accepted the EULA terms. In one embodiment, the user will be presented with a EULA screen 600 each time the user accesses the mobile application 106. In another embodiment, the user will be presented with a EULA screen 600 the first time the user accesses the mobile application 106 and, thereafter, may never be presented with it again or may intermittently be presented with the EULA screen 600.

As illustrated in the dashboard interface 700 illustrated in FIG. 7, some embodiments of the disclosed system may include a dashboard or summary GUI 700 that displays an information summary regarding compliance and non-compliance across all caregiver's patient interactions. The dashboard GUI 700 may enable users to view information over various time periods. For example, the user may be able to select whether to view information from today, yesterday, the previous seven days, the current month, the previous month, the current year, the last year, or any other time period.

The dashboard GUI 700 may also indicate compliance percentages for the selected time period and, in some embodiments, may compare the selected time period against a yearly pre-defined compliance level. If the selected time period is below the yearly pre-defined compliance level, the dashboard GUI 700 may alert the user by, for example, changing the color, font, or text size of the text disclosing the selected time period's compliance percentage.

In addition to compliance percentages, the dashboard GUI 700 may include a bar chart, such as that displayed in FIG. 7, illustrating compliance and non-compliance in bar form. To distinguish between compliance and non-compliance bars, different colors or patterns may be used. For clarity, the compliance and non-compliant totals may be shown below or above the chart along with the corresponding percentage.

In some embodiments, if a user desires to see more detailed information, the user can interact with the dashboard GUI 700 by selecting compliance or non-compliance cells, which navigate the user to the compliance/non-compliance interaction details GUI 800 and display the appropriate data.

Figure 18:
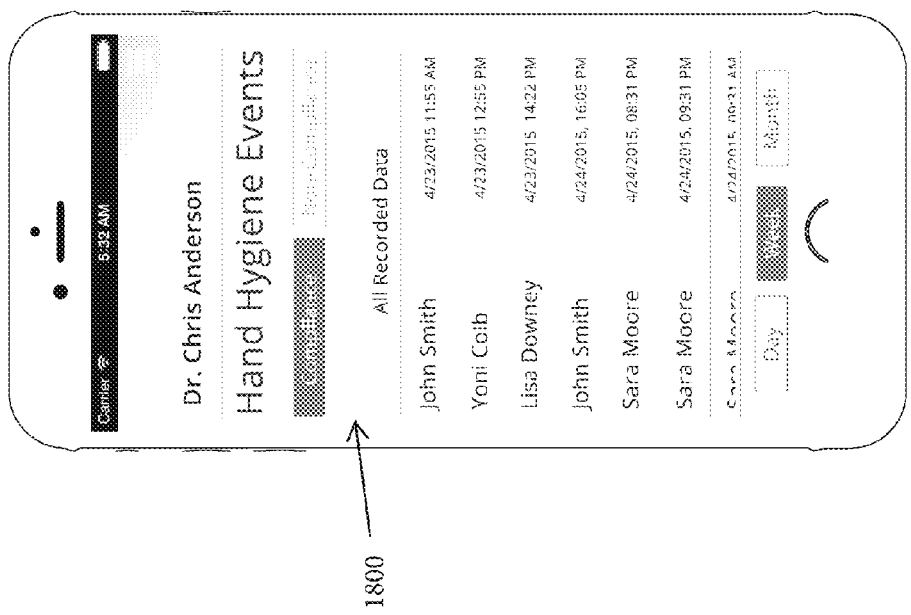
FIG. 18 is an example graphical user interface showing a mobile interface compliance list screen according to one embodiment of the present disclosure.

At the compliance/non-compliance interaction details interface 800, the mobile application 106 illustrates details of interactions with patients, as illustrated in FIG. 8. More specifically, the interface 800, 1800 may display a list of the compliant and non-compliant interactions with patients, with each patient's identifying information in an interaction cell, as illustrated in FIG. 18. In a preferred embodiment, the mobile application 106 will include a patient's medical record number in place of the patient's name. For example, each interaction cell may include a patient's name and the date and time of the patient's last interaction with a caregiver.

In some embodiments, the compliance/non-compliance interaction details interface 800 may have two lists, a first list for compliant interactions and a second list for non-compliant interactions. These lists may be on the same interface, or the mobile application 106 may enable the user to toggle between the lists. The compliance/non-compliance interaction details interface 800 may also have a navigation feature that enables a user to leave the interface 800. For example, the compliance/non-compliance interaction details GUI 800 may have a "back" button that can bring up the dashboard GUI 700.

Figure 19:
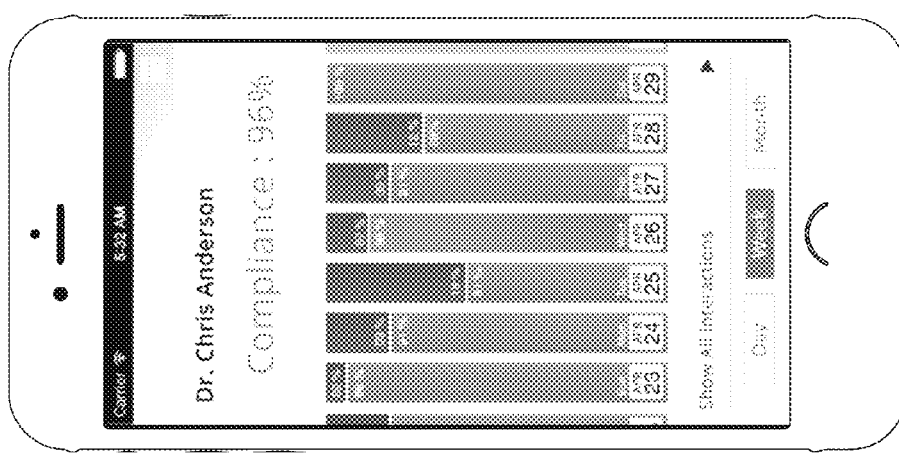
FIG. 19 is an example graphical user interface showing a mobile interface compliance graph screen according to one embodiment of the present disclosure.

As with the dashboard GUI 700, and as illustrated in FIG. 19, the compliance/non-compliance interaction details GUI 800 may enable users to view information over various time periods. For example, the user may be able to select whether to view information from today, yesterday, the previous seven days, the current month, the previous month, the current year, the last year, or any other time period. In some embodiments, selection of a time period may be available through use of a tab-bar or scroller on the bottom of the interface 800.

Management of the system may require master administrators and administrators. In some embodiments, permissions are granted to master administrators in order to manage other administrators, manage hospital or other care facility information, to update beacons order and supply, and to generate reports. General parameters provided for the system are yearly compliance rates based on the definitions that may be provided by the Center for Disease Control (CDC).

In addition to the master administrator, other types of administrators in the system may be IDSSS management system administrators and managed care administrators. The system may enable a master administrator to, in some embodiments, add/edit/remove IDSSS management system administrators and add/edit/remove managed care administrators such as insurance companies, Medicare, Medicaid, etc., and may be limited to read-only access.

In addition to managing system and care administrators, the system may also enable master administrators to manage hospital information by enabling add/remove/edit options for hospital information such as, but not limited to, hospital name, address, phone number, email address, contact full name, contact phone number, and contact email address. Additionally, the system may enable management of hospital information by enabling add/remove/edit options for hospital administrator information (i.e., infection disease dept. chief) such as, but not limited to, name, surname, phone number, and email address.

In regard to permissions, a hospital administrator, configured by the IDSSS management system administrator, can create various hospital sub-administrators and can provide one or more permissions to each hospital sub-administrator. These permissions can include, but are not limited to, accessing a mobile application 106 for pairing with a patient's wristband with beacon 104 and access to a web interface.

In addition to managing other administrators and hospital information, the system may further enable the master administrator to update beacon order and supply. More specifically, a master administrator may be able to record a beacon order (for example, patient wristband beacon 104 or dispenser beacon 102) or may be able to record beacon shipping (for example, patient wristband beacon 104 or dispenser beacon 102).

The system may also generate inter-hospital reports that can be exported into PDF and XLS formats. The reports can include a visual overview of the information by including graphs or charts. In one embodiment, the reports can show how many beacons of every type (i.e., patient 104 and dispenser 102) have been ordered and provided to every hospital, how many patient beacons 104 have been activated, and the number of caregivers and account creations.

The reports may be searchable by allowing cross-reference querying of any one or more of predetermined parameters together with a time period selector. Some of the parameters may include, but are not limited to, hospital name, caregiver type, caregiver name, caregiver surname, caregiver employee number, patient name, patient surname, patient medical record number, and compliant/non-compliant/both status.

In some embodiments, the system can auto-generate inter-hospital reports such as, but not limited to, daily, weekly, monthly, and yearly non-compliance reports that are grouped by hospital and sorted by number of non-compliances (for example, highest on top). Report data can include all hospital, caregiver, and patient information as well as timestamps of non-compliance events. Further, reports can include hospital compliance percentages and can include a visual overview of the information by including graphs or charts. To manage who sees the information, the system may allow management of email addresses that receive the auto-generated reports.

For each hospital, the system may create intra-hospital reports and may allow cross-reference querying of any one or more parameters together with a time period selector. The parameters may include caregiver type, caregiver name, caregiver surname, caregiver employee number, patient name, patient surname, patient medical record number, and compliant/non-compliant/both status. Additionally, the system can export these reports in PDF and XLS formats.

Figure 16:
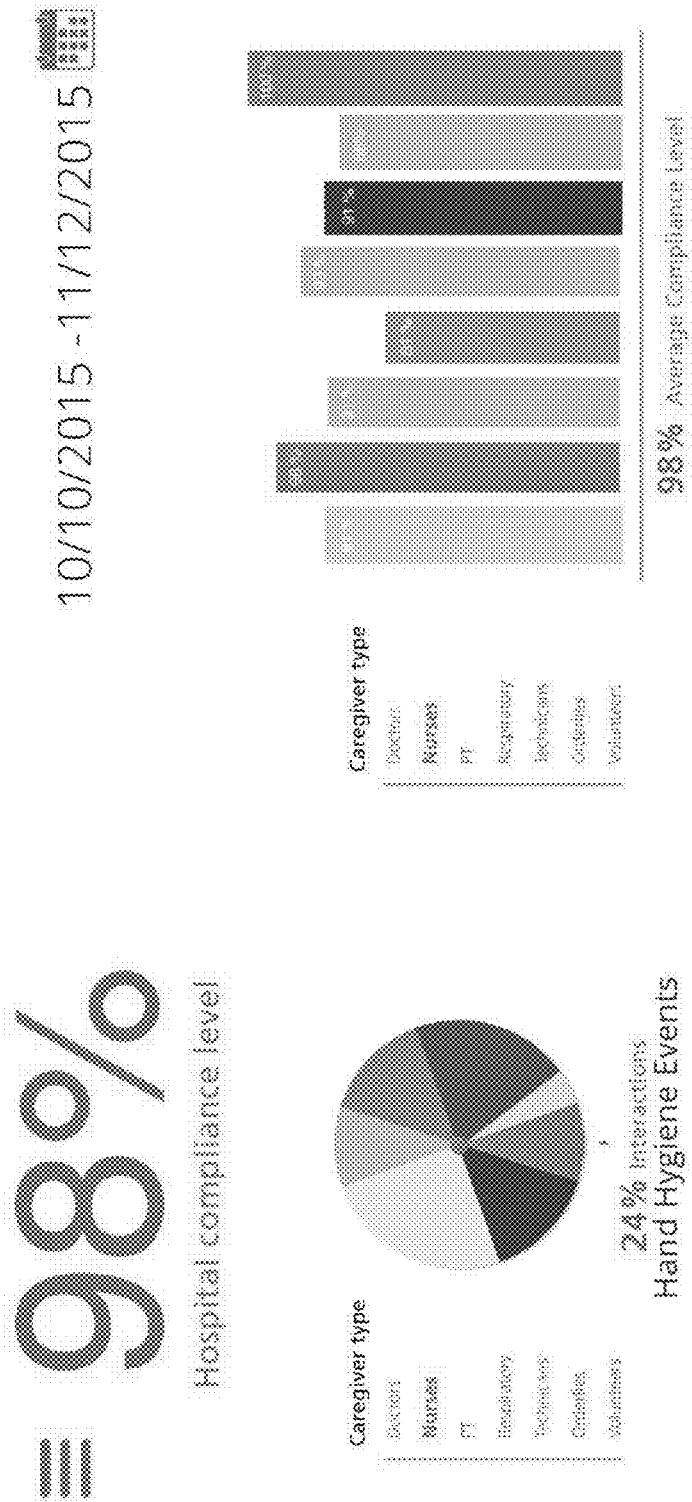
FIG. 16 is an exemplary hospital report that includes a visual overview of the information in the form of graphs.
Figure 17:
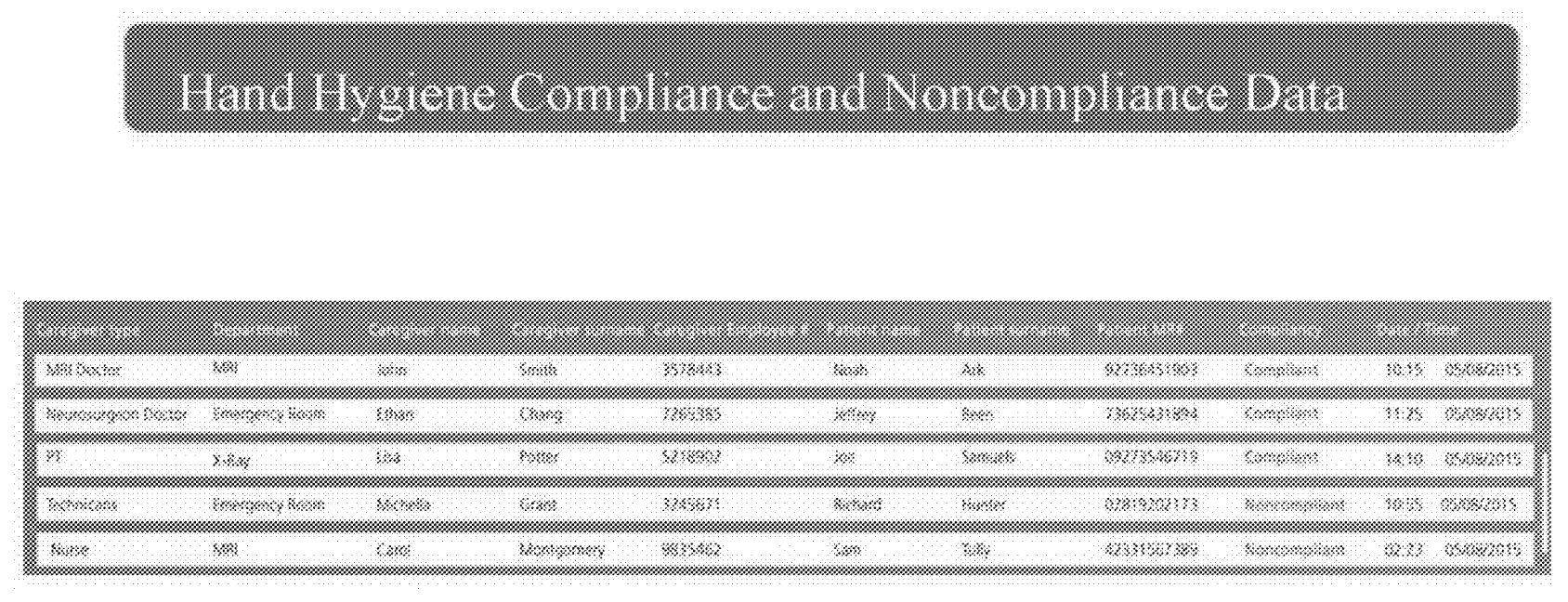

In some embodiments, the system can auto-generate intra-hospital reports such as, but not limited to, daily, weekly, monthly, and yearly non-compliance reports that are grouped by caregiver and sorted by number of non-compliances (for example, highest on top). Report data can include all caregiver and patient information as well as timestamps of non-compliance events. Further, reports can include a visual overview of the information by including graphs or charts, as illustrated in FIGS. 16 and 17, and the number of caregivers and system usage. To manage who sees the information, the system may allow management of email addresses that receive the auto-generated reports.

In addition to inter- and intra-hospital reports, the system may create reports for each doctor. These reports can be generated (automatically or by request) to track non-compliance on a daily, weekly, monthly, or yearly basis. Report data can include all patient information as well as timestamps of non-compliance events. Further reports can include a visual overview of the information by including graphs or charts, as illustrated in FIGS. 18 and 19. In a preferred embodiment, the system will include a patient's medical record number in place of the patient's name.

In some embodiments, the system has a native interface for patient/wristband matching and may be developed for smartphones that support Bluetooth low energy protocol (BLE). Patient data input and bracelet pairing may include information such as, but not limited to, patient name, patient surname, patient medical record number, ability to pair with the beacon/wristband 104, and status of patient (for example, notification when the patient is released and the wristband 104 is decommissioned).

Since the dispenser beacon 102 requires power, such as a battery, a feature may be included in the beacon 102 that can test the beacon battery level. While batteries for these beacons 102 should last for an extended period of time due to the fact that these beacons 102 only broadcast during washing or dispensing, the battery level may need periodic testing. Therefore, hospital staff can use this mode for periodic testing of faucet and dispenser beacons' battery level.

In some embodiments, the system can be at least partially implemented on a mobile device as a mobile application 106. In other embodiments, the system can be at least partially implemented on a web-based interface. In either version, the system can accept input of information regarding a caregiver's name, surname, employee number, email address, and position type (for example, doctor, nurse, PT, respirator, technician, orderly, volunteer, etc.).

Preferably, the system can support bulk ingestion of caregiver data using pre-defined Excel or CSV formats as well as allowing add/edit/remove/suspend functionality. In some embodiments, the system can send auto-generated passwords to caregivers' emails, and caregivers can use their employee number as a username and password in order to login to the mobile application 106. Additionally, in further embodiments, a specific GUI may be dedicated for hospitals and administrators to use in order to provide feedback and manage previously provided feedback.

Various types of hardware can be used to implement the disclosed components of the system. The main components, in a preferred embodiment, are patient wristbands, soap/sanitizer dispensers, and beacons designed specifically for patient wristbands 104 and for soap/sanitizer dispensers 102. The beacons for patient wristbands 104 and soap/sanitizer dispensers 102 may be identical or may vary.

For example, the system preferably will include the use of Bluetooth enabled patient wristbands 104 and disinfectant dispensers 102, such as, but not limited to, soap or sanitizer. In some embodiments, the beacons 102, 104 will be Bluetooth low energy (BLE) compliant. The beacons 102, 104 can broadcast UUID, major and minor values. Additionally, the beacons 102, 104 can have the same UUID, which will be unique and different from those found on common beacon brands. The minor value on every beacon 102, 104 may be different and should, in a preferred embodiment, be numbered continuously starting with one. Broadcast power, RSSI, is preferably configurable. Additionally, the Bluetooth module address may be unique and all beacons 102, 104 may have as long an identical prefix as possible (i.e., out of the 12 numeric/letters, the first 6 will be identical on all beacons 102, 104).

For patient wristbands/hospital bracelets, the wristband/bracelet may be plastic, disposable, inexpensive to make, MRI-safe (or have titanium cover for use in an MM), include a beacon 104, and, as is standard with hospital admittance bracelets, have the patient's name and medical record number label. More specifically, the beacon 104 may be attached to one of the various holes in the bracelet that are common to hospital bracelets. Alternatively, the beacon 104 may be embedded in the bracelet or otherwise attached to the bracelet.

The disinfectant (i.e. soap or sanitizer) dispenser beacon 102 may have at least 10 seconds of current in order for the application to pick up on the broadcast and register cleansing action. Further, the dispenser may have a built-in visual countdown timer that counts down from a predetermined number (for example, 10) to 0. Caregivers can be instructed to stay adjacent to the dispenser until the countdown reaches 0 in order to prevent a finding of non-compliance. In some embodiments, the beacon broadcast strength is low enough so that the application only picks it up in a radius of up to 3-4 feet from the dispenser.

Figure 20:
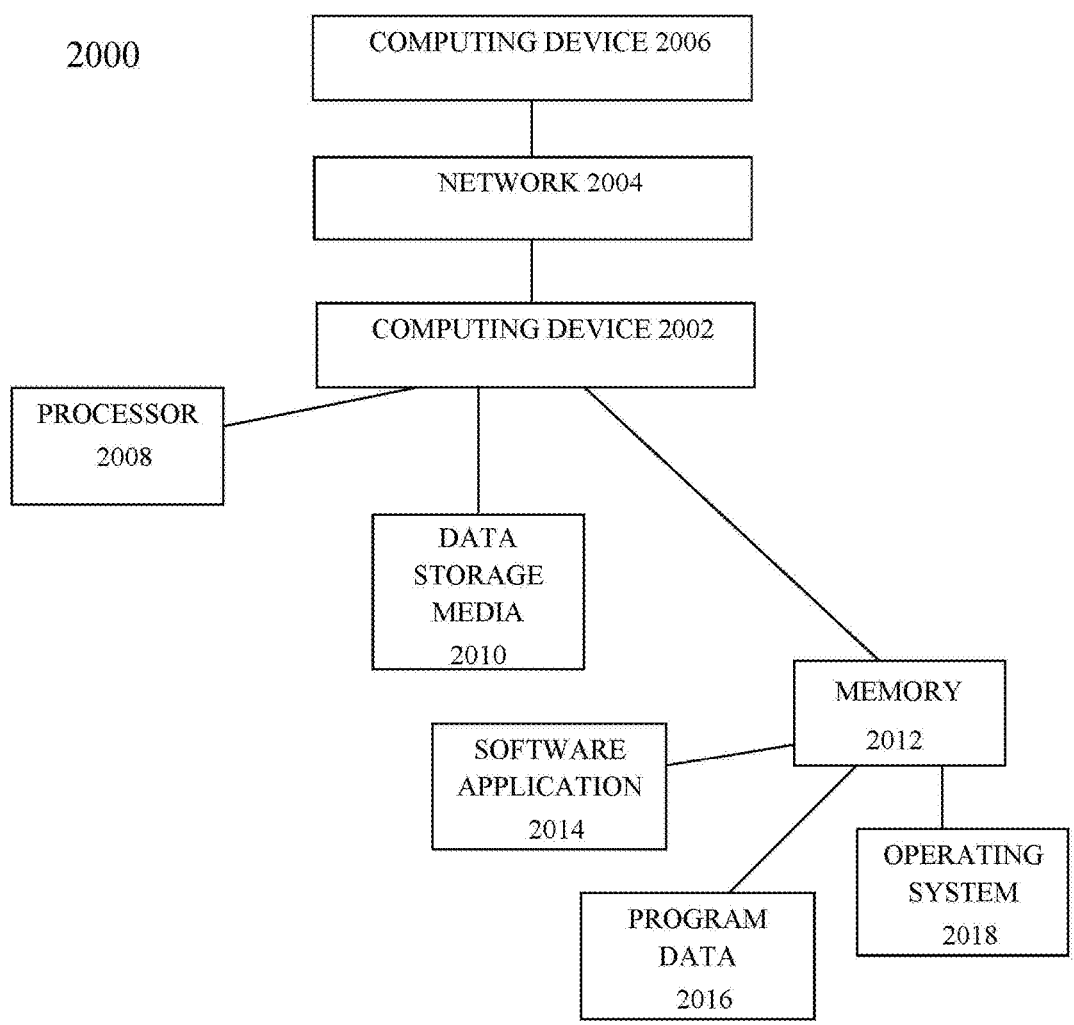
FIG. 20 is a schematic block diagram depicting an example computing system used in accordance with one embodiment of the present invention.

In some embodiments, the system described herein uses one or more computing systems to carry out the various functions described herein. FIG. 20 is a schematic block diagram of an example computing system 2000. The example computing system 2000 includes at least one computing device 2002. In some embodiments, the computing system 2000 further includes a communication network 2004 and one or more additional computing devices 2006 (such as a server).

The computing device 2002 can be located in a user's home or other place of business. In some embodiments, computing device 2002 is a mobile device. The computing device 2002 can be a stand-alone computing device or a networked computing device that communicates with one or more other computing devices 2006 across a network 2004. The additional computing device(s) 2006 can be, for example, located remotely from the first computing device 2002, but configured for data communication with the first computing device 2002 across a network 2004.

In some examples, the computing devices 2002 and 2006 include at least one processor or processing unit 2008 and system memory 2012. The processor 2008 is a device configured to process a set of instructions. In some embodiments, system memory 2012 may be a component of processor 2008; in other embodiments system memory 2012 is separate from the processor 2008. Depending on the exact configuration and type of computing device, the system memory 2012 may be volatile (such as RAM), non-volatile (such as ROM, flash memory, etc.) or some combination of the two. System memory 2012 typically includes an operating system 2018 suitable for controlling the operation of the computing device 2002, such as the WINDOWS® operating systems or the OS X operating system, or a server, such as Windows SharePoint Server, also from Microsoft Corporation, or such as a Mac Mini with OS X. The system memory 2012 may also include one or more software applications 2014 and may include program data 2016.

The computing device 2002 may have additional features or functionality. For example, the computing device 2002 may also include additional data storage devices 2010 (removable and/or non-removable) such as, for example, magnetic disks, optical disks, or tape. Computer storage media 2010 may include volatile and nonvolatile, removable and non-removable media implemented in any method or technology for storage of information, such as computer readable instructions, data structures, program modules, or other data. System memory, removable storage, and non-removable storage are all examples of computer storage media. Computer storage media 2010 includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium that can be used to store the desired information and that can be accessed by the computing device 2002. An example of computer storage media 2010 is non-transitory media.

In some examples, one or more of the computing devices 2002 and 2006 can be located in an establishment, such as a hospital, healthcare facility, or nursing home. In other examples, the computing device 2002 can be a personal computing device that is networked to allow the user to access and utilize the system disclosed herein from a remote location, such as in a user's home, office or other location. In some embodiments, the computing device 2002 is a smart phone tablet, laptop computer, personal digital assistant, or other mobile device. In some embodiments, system operations and functions are stored as data instructions for a smart phone application. A network 2004 facilitates communication between the computing device 2002 and one or more servers, such as an additional computing device 2006, that hosts the system. The network 2004 may be a wide variety of different types of electronic communication networks. For example, the network 2004 may be a wide-area network, such as the Internet, a local-area network, a metropolitan-area network, or another type of electronic communication network. The network 2004 may include wired and/or wireless data links. A variety of communications protocols may be used in the network 2004 including, but not limited to, Wi-Fi, Ethernet, Transport Control Protocol (TCP), Internet Protocol (IP), Hypertext Transfer Protocol (HTTP), SOAP, remote procedure call protocols, and/or other types of communications protocols.

In some examples, the additional computing device 2006 is a Web server. In this example, the first computing device 2002 includes a Web browser that communicates with the Web server to request and retrieve data. The data is then displayed to the user, such as by using a Web browser software application. In some embodiments, the various operations, methods, and functions disclosed herein are implemented by instructions stored in memory. When the instructions are executed by the processor 2008 of the one or more computing devices 2002 or 2006, the instructions cause the processor 2008 to perform one or more of the operations or methods disclosed herein.

The accompanying specification and drawings only illustrate an exemplary embodiment of a system of communicating the monitoring and alerting of healthcare workers to help prevent spread of infectious disease, as well as the system's constituent parts and associated methods and processes. However, other exemplary embodiments are possible, and the drawings and specification are not intended to be limiting in that regard. Thus, although the description above and accompanying drawings contains much specificity, the details provided should not be construed as limiting the scope of the embodiment(s) but merely as providing illustrations of some of the presently preferred embodiment(s).

The drawings and description are not to be taken as restrictive on the scope of the embodiment(s) and are understood as broad and general teachings in accordance with the present invention. While the present embodiment(s) of the invention have been described using specific terms, such description is for present illustrative purposes only, and it is to be understood that modifications and variations to such embodiments, including but not limited to the substitutions of equivalent features, materials, or parts, and the reversal of various features thereof, may be practiced by those of ordinary skill in the art without departing from the spirit and scope of the invention. By the same token, it should be appreciated that certain terms may be utilized interchangeably, such as "caregiver" and "healthcare worker," "hospital" and "facility" and the like. Unless otherwise stated, these terms should be interpreted so as to impart the broadest scope without departing from the spirit and scope of the invention.

What is claimed is:

1. A system to assist in the prevention of transfer of infectious disease, comprising:
a patient wristband having a first Bluetooth beacon, wherein the patient wristband is attached to a patient and contains personal identifier information of the patient;
a disinfectant dispenser having a second Bluetooth beacon; and
a mobile application on a mobile computing device that is enabled to communicate with the patient wristband beacon and the disinfectant dispenser beacon, wherein:
the patient wristband beacon is enabled to broadcast a signal;
the mobile application, which is associated with a caregiver, is enabled to scan for, and detect, a patient wristband beacon signal and determine a distance between the patient wristband beacon and the mobile computing device using a global positioning system or a wireless tracking system;
the disinfectant dispenser beacon is enabled to broadcast a signal when the disinfectant dispenser is used;
the mobile application is enabled to scan for, and detect, the disinfectant dispenser beacon broadcast signal;
the mobile application is enabled to report the patient wristband beacon signal detection, the distance between the patient wristband beacon and the mobile computing device, and the disinfectant dispenser beacon signal detection to a cloud storage system for storage and analysis, wherein analysis determines:
whether a predetermined amount of time has elapsed between use of the disinfectant dispenser and detection of the patient wristband beacon; and
whether the distance between the patient wristband beacon and the mobile computing device is less than a predetermined distance;
the mobile application is configured to activate the mobile computing device to cause the mobile computing device to emit an approach alert if the predetermined amount of time has elapsed and the distance between the patient wristband beacon and the mobile computing device is less than the predetermined distance; and
the mobile application is configured to activate the mobile computing device to cause the mobile computing device to emit a departure alert if the distance between the patient wristband beacon and the mobile computing device is, at a first time, less than the predetermined distance and, at a later time, more than a second predetermined distance.

2. A method of preventing transfer of infectious disease, the method comprising:
using a mobile device having a mobile application to pair a patient wristband beacon with a patient, wherein the mobile device is associated with a caregiver and is enabled to:
detect one or more Bluetooth beacons;
display the one or more detected beacons on a screen of the mobile device;
receive a selection of a first of the one or more detected beacons, the first selected beacon having a unique identifier;
receive patient information associated with the patient;
pair the selected first beacon with the patient information; and
store the selected first beacon and the patient information in a database;
wherein the patient wristband beacon is embedded in a patient wristband, and the patient wristband beacon is comprised of the selected first beacon;
detecting when the caregiver has used or activated a disinfectant dispenser to disinfect the caregiver's hands, wherein the mobile device is enabled to:
detect a second Bluetooth beacon having a predefined unique identifier associated with the disinfectant dispenser, the second beacon broadcasting a signal when the disinfectant dispenser is used;
create a note of compliance comprised of a date and a time associated with detection of the second beacon; and
store the note of compliance in the database;
alerting the caregiver to disinfect the caregiver's hands before approaching the patient, wherein the mobile device is enabled to:
detect the patient wristband beacon;
calculate an approach distance between the caregiver and the patient;
determine whether the calculated approach distance between the caregiver and the patient is less than a predetermined approach distance;
calculate an approach elapsed time, wherein the approach elapsed time is a time difference between a time associated with detection of the patient wristband beacon and the time associated with the stored note of compliance;
determine whether the calculated approach elapsed time is greater than a predetermined approach elapsed time;
alert the caregiver with an approach alert that the calculated approach elapsed time is greater than the predetermined approach elapsed time, and the calculated approach distance between the caregiver and the patient is less than the predetermined approach distance;
create a note of non-compliance comprised of a date and a time associated with occurrence of the approach alert; and
store the note of approach non-compliance in the database;
alerting the caregiver to disinfect the caregiver's hands while the caregiver is with the patient, wherein the mobile device is enabled to:
determine whether a calculated stationary distance between the caregiver and the patient is less than the predetermined approach distance;
determine when a most recent note of compliance has been stored in the database;
calculate a stationary elapsed time, wherein the stationary elapsed time is a time difference between the time associated with detection of the patient wristband beacon and a time associated with the stored most recent note of compliance;
determine whether the calculated stationary elapsed time is greater than the predetermined approach elapsed time;
alert the caregiver with a stationary alert that the calculated stationary elapsed time is greater than the predetermined approach elapsed time, and the calculated stationary distance between the caregiver and the patient is less than the predetermined approach distance;
create a note of non-compliance comprised of a date and a time associated with occurrence of the stationary alert; and
store the note of stationary non-compliance in the database;
alerting the caregiver to disinfect the caregiver's hands after departing from the patient, wherein the mobile device is enabled to:
calculate a departure distance between the caregiver and the patient;
determine whether the calculated departure distance between the caregiver and the patient is more than a predetermined departure distance;
calculate a departure elapsed time, wherein the departure elapsed time is a time difference between the time associated with detection of the patient wristband beacon and current time;
determine whether the calculated departure elapsed time is greater than a predetermined departure elapsed time;
alert the caregiver with a departure alert that the calculated departure elapsed time is greater than the predetermined departure elapsed time, and the calculated distance between the caregiver and the patient is more than the predetermined departure distance;
create a note of non-compliance comprised of a date and a time associated with occurrence of the departure alert; and
store the note of departure non-compliance in the database;
alerting the caregiver to disinfect the caregiver's hands after departed from the patient, wherein the mobile device is enabled to:
calculate a departed distance between the caregiver and the patient, wherein the departed distance is further than the departure distance;
determine whether the calculated departed distance between the caregiver and the patient is more than a predetermined departed distance;
alert the caregiver with a departed alert that the calculated departure elapsed time is greater than the predetermined departure time, and the calculated distance between the caregiver and the patient is more than the predetermined departed distance;
create a note of non-compliance comprised of a date and a time associated with occurrence of the departed alert; and
store the note of departed non-compliance in the database;
alerting the caregiver to disinfect the caregiver's hands if the caregiver is in a vicinity of a plurality of patients, wherein the mobile device is enabled to:
detect a plurality of patient wristband beacons;
calculate a multi-patient distance between the caregiver and at least one of the plurality of detected patient wristband beacons;
determine whether the calculated multi-patient distance between the caregiver and the at least one of the plurality of patient wristband beacons is less than a predetermined multi-patient distance;
calculate a multi-patient elapsed time, wherein the multi-patient elapsed time is a time difference between a time associated with detection of the plurality of patient wristband beacons and current time;
alert the caregiver with a multi-patient alert that the calculated multi-patient elapsed time is greater than a predetermined multi-patient elapsed time, and the calculated multi-patient distance between the caregiver and the plurality of patient wristband beacons is less than the predetermined multi-patient distance;
create a note of non-compliance comprised of a date and a time associated with occurrence of the multi-patient alert; and
store the note of multi-patient non-compliance in the database; and tracking compliance and non-compliance using the mobile application on the mobile device, wherein the mobile application is configured to:
    store each created note of compliance for the caregiver;
    store each created note of non-compliance for the caregiver, wherein notes of non-compliance are comprised of approach non-compliance, stationary non-compliance, departure non-compliance, departed non-compliance, and multi-patient non-compliance;
    analyze the stored notes of compliance and non-compliance;
    summarize the analysis of the stored notes of compliance and non-compliance according to date;
    determine compliance percentages based on a comparison of compliance notes to total interactions and non-compliance notes to total interactions, wherein total interactions are a total number of detected patient wristband beacons; and
    summarize the compliance percentages.

3. A method of preventing transfer of infectious disease, the method comprising:
    using a mobile device to pair a patient wristband beacon with a patient, wherein the mobile device is enabled to store a mobile application and is associated with a caregiver;
    detecting when a caregiver has used a disinfectant dispenser to disinfect the caregiver's hands;
    alerting the caregiver to disinfect the caregiver's hands before approaching the patient, wherein the mobile device is enabled to:
        detect the patient wristband beacon;
        calculate an approach distance between the caregiver and the patient;
        determine whether the calculated approach distance between the caregiver and the patient is less than a predetermined approach distance;
        calculate an approach elapsed time, wherein the approach elapsed time is a time difference between a time associated with detection of the patient wristband beacon and a time associated with a previously stored note of hand washing compliance;
        determine whether the calculated approach elapsed time is greater than a predetermined approach elapsed time;
        alert the caregiver with an approach alert that the calculated approach elapsed time is greater than the predetermined approach elapsed time, and the calculated approach distance between the caregiver and the patient is less than the predetermined approach distance;
        create a note of non-compliance comprised of a date and a time associated with occurrence of the approach alert; and
        store the note of approach non-compliance in the database;
    alerting the caregiver to disinfect the caregiver's hands while with the patient;
    alerting the caregiver to disinfect the caregiver's hands after departing from the patient;
    alerting the caregiver to disinfect the caregiver's hands after departed from the patient;
    alerting the caregiver to disinfect the caregiver's hands when the caregiver is in a vicinity of a plurality of patients;
    tracking the caregiver's compliance and non-compliance with the alerts using the mobile application on the mobile device; and
    generating compliance reports using the mobile application on the mobile device.

4. The method of claim 3, wherein the mobile device is enabled to:
    detect one or more Bluetooth beacons;
    display the one or more detected beacons on a screen of the mobile device;
    receive a selection of one of the one or more detected beacons, the selected beacon having a unique identifier;
    receive patient information associated with the patient;
    pair the selected beacon with the patient information; and
    store the selected beacon and the patient information in a database;
    wherein the patient wristband beacon is embedded in a patient wristband and the patient wristband beacon is comprised of the selected beacon.

5. The method of claim 3, wherein the mobile device is enabled to:
    detect a Bluetooth beacon having a predefined unique identifier associated with the disinfectant dispenser, the beacon being activated and broadcasting a signal when the disinfectant dispenser is used;
    create the note of hand washing compliance comprised of a date and the time associated with detection of the disinfectant dispenser beacon; and
    store the note of compliance in the database.

6. The method of claim 3, wherein the mobile device is enabled to:
    determine whether a calculated stationary distance between the caregiver and the patient is less than a predetermined approach distance;
    determine when a most recent note of compliance has been stored in a database;
    calculate a stationary elapsed time, wherein the stationary elapsed time is a time difference between a time associated with detection of the patient wristband beacon and a time associated with the stored most recent note of compliance;
    determine whether the calculated stationary elapsed time is greater than the predetermined approach elapsed time;
    alert the caregiver with a stationary alert that the calculated stationary elapsed time is greater than the predetermined approach elapsed time, and the calculated stationary distance between the caregiver and the patient is less than the predetermined approach distance;
    create a note of non-compliance comprised of a date and a time associated with occurrence of the stationary alert; and
    store the note of stationary non-compliance in the database.

7. The method of claim 3, wherein the mobile device is enabled to:
    detect the patient wristband beacon;
    calculate a departure distance between the caregiver and the patient;
    determine whether the calculated departure distance between the caregiver and the patient is more than a predetermined departure distance;
    calculate a departure elapsed time, wherein the departure elapsed time is a time difference between a time associated with detection of the patient wristband beacon and current time;

determine whether the calculated departure elapsed time is greater than a predetermined departure elapsed time;

alert the caregiver with a departure alert that the calculated departure elapsed time is greater than the predetermined departure elapsed time and the calculated distance between the caregiver and the patient is more than the predetermined departure distance;

create a note of non-compliance comprised of a date and a time associated with occurrence of the departure alert; and store the note of departure non-compliance in the database.

8. The method of claim 7, wherein the mobile device is enabled to:

calculate a departed distance between the caregiver and the patient, wherein the departed distance is further than the departure distance;

determine whether the calculated departed distance between the caregiver and the patient is more than a predetermined departed distance;

alert the caregiver with a departed alert that the calculated departure elapsed time is greater than the predetermined departure elapsed time, and the calculated departed distance between the caregiver and the patient is more than the predetermined departed distance;

create a note of non-compliance comprised of a date and a time associated with occurrence of the departed alert; and store the note of departed non-compliance in a database.

9. The method of claim 3, wherein the mobile device is enabled to:

detect a plurality of patient wristband beacons;

calculate a multi-patient distance between the caregiver and at least one of the plurality of detected patient wristband beacons;

determine whether the calculated multi-patient distance between the caregiver and the at least one of the plurality of patient wristband beacons is less than a predetermined multi-patient distance;

calculate a multi-patient elapsed time, wherein the multi-patient elapsed time is a time difference between a time associated with detection of the plurality of patient wristband beacons and current time; and alert the caregiver with a multi-patient alert that the calculated multi-patient elapsed time is greater than a predetermined multi-patient elapsed time, and the calculated multi-patient distance between the caregiver and the plurality of patient wristband beacons is less than the predetermined multi-patient distance;

create a note of non-compliance comprised of a date and a time associated with occurrence of the multi-patient alert; and store the note of multi-patient non-compliance in the database.

10. The method of claim 3, wherein the mobile application is configured to:

store each created note of compliance for the caregiver;

store each created note of non-compliance for the caregiver;

analyze the stored notes of compliance and non-compliance;

summarize the analysis of the notes of compliance and non-compliance according to date;

determine compliance percentages based on a comparison of compliance notes to total interactions and non-compliance notes to total interactions, wherein total interactions are a total number of detected patient wristband beacons; and summarize the compliance percentages.

* * * * *